United States Patent [19]
Knauf-Beiter et al.

[11] Patent Number: 6,136,816
[45] Date of Patent: Oct. 24, 2000

[54] METHOD FOR PROTECTING POME PLANTS AGAINST VENTURIA AND PODOSPHEAREA SPP. INFESTATION

[75] Inventors: Gertrude Knauf-Beiter, Müllheim, Germany; Hans Steiner, Rheinfelden, Switzerland

[73] Assignee: Novartis Crop Protection, Inc., Greensboro, N.C.

[21] Appl. No.: 09/171,073

[22] PCT Filed: Mar. 29, 1997

[86] PCT No.: PCT/EP97/01599

§ 371 Date: Oct. 9, 1998

§ 102(e) Date: Oct. 9, 1998

[87] PCT Pub. No.: WO97/37535

PCT Pub. Date: Oct. 16, 1997

[30] Foreign Application Priority Data

Apr. 11, 1996 [CH] Switzerland ................ 915/96

[51] Int. Cl.$^7$ .......... A01N 43/50; A01N 43/54; A01N 43/64
[52] U.S. Cl. .......... 514/275; 514/383; 514/391
[58] Field of Search .......... 514/275, 383, 514/391

[56] References Cited

U.S. PATENT DOCUMENTS

| | | | |
|---|---|---|---|
| 4,931,560 | 6/1990 | Hubele | 544/315 |
| 4,997,941 | 3/1991 | Hubele | 544/332 |
| 5,153,200 | 10/1992 | Hubele | 514/275 |
| 5,403,844 | 4/1995 | Mittermeier et al. | 514/275 |
| 5,430,035 | 7/1995 | Zeun et al. | 514/275 |
| 5,508,283 | 4/1996 | Eicken et al. | 514/275 |
| 5,536,726 | 7/1996 | Zeun et al. | 514/275 |
| 5,567,705 | 10/1996 | Mittermeier et al. | 514/272 |
| 5,589,479 | 12/1996 | Eicken et al. | 514/275 |
| 5,591,747 | 1/1997 | Eicken et al. | 514/275 |
| 5,599,828 | 2/1997 | Zeun et al. | 514/383 |

FOREIGN PATENT DOCUMENTS

| | | |
|---|---|---|
| 151404 | 10/1981 | Germany . |
| 2 267 644 | 12/1993 | United Kingdom . |

OTHER PUBLICATIONS

Hickey, K.D. et al., Fungic. Nematic. Tests, vol. 51. "Disease incidence on 'Rome Beauty' apple treated seasonally with fungicides applied airblast at 50 gpa in 1995", p. 8 (1996)(see abstract No. 97–81250) Database Cropu.

Pscheidt, J.W. et al., Fungic. Nematic. Tests, vol. 50. "Efficacy of fungicides for control of apple scab and powdery mildew" p. 23, (1995) (see abstract No. 96–81128) Database Cropu.

Ritchie, D.F. et al., Fungic. Nematic.Tests, vol. 50, "Evaluation of Orbit and CGA–219417 for control of brown rot on peach", p. 59 (1995).

Tomlin, C., The Pesticide Manual, Tenth Edition, British Crop Protection Council Farnham, see pp. 885, 886, 1336, "anilinopyrimidine", 161 and 162.

Wilcox, W.F. et al., Fungic. Nematic. Tests, vol. 51, "Evaluation of Fungicides and Spray Timings for Control of Botrytis Bunch Rot of Grapes" p. 73, line 5–6 (1995).

Derwent Abstracts, 82–03995E [03] WPIDS (for patent application DD–151 404) (1981).

*Primary Examiner*—Allen J. Robinson
*Attorney, Agent, or Firm*—Michael P. Morris; William A. Teoli, Jr.

[57] ABSTRACT

This invention relates to fungicidal active ingredient mixtures comprising at least two active ingredient components together with a suitable carrier material, wherein component I is cyprodinil [=2-anilino-4-cyclopropyl-6-methylpyrimidine] and wherein component II is A) myclobutanil [=2-p-chlorophenyl-2-(1H-1,2,4-triazol-1-ylmethyl) hexanenitrile]; or B) iprodione [=3-(3,5-dichlorophenyl)-N-isopropyl-2,4-dioxoimidazolidine-1-carboxamide], and to methods of using such mixtures in crop protection, especially in the control and prevention of disease infestation.

2 Claims, No Drawings

METHOD FOR PROTECTING POME PLANTS AGAINST VENTURIA AND PODOSPHEAREA SPP. INFESTATION

This application is a 371 of PCT/EP97/01599, filed Mar. 29, 1997.

The present invention relates to fungicidal active ingredient mixtures having synergistically enhanced action and to methods of using such mixtures in crop protection, especially in the control and prevention of disease infestation.

The mixtures according to the invention comprise at least two active ingredient components together with a suitable carrier material, wherein component I is cyprodinil [=2-anilino-4-cyclopropyl-6-methyl-pyrimidine] (formula I) (reference: EP-A-310 550);

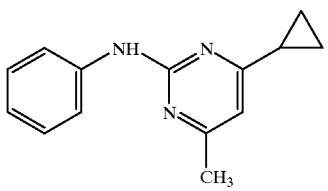

and wherein component II is

A) myclobutanil [=2-p-chlorophenyl-2-(1H-1,2,4-triazol-1-ylmethyl)hexanenitrile] (reference: C. Tomlin (editor): The Pesticide Manual, 10th edition, Farnham, UK, 1994, No. 489); or B) iprodione [=3-(3,5-dichlorophenyl)-N-isopropyl-2,4-dioxoimidazolidine-1-carboxamide] (reference: C. Tomlin (editor): The Pesticide Manual, 10th edition, Farnham, UK, 1994, No. 410).

Synergistic fungicidal active ingredient mixtures of pyrimethanil [2-anilino-4,6-dimethylpyrimidine] with myclobutanil and with iprodione are known from GB 2 267 644.

It has now been found that the mixtures according to the invention have very advantageous properties for protecting plants against disease infestation.

The invention relates also to salts and metal complexes of compounds I and II. Among the acids that can be used for the preparation of salts of formula I or II there may be mentioned:

hydrohalic acids, such as hydrochloric acid or hydrobromic acid, sulfuric acid, phosphoric acid, nitric acid, and organic acids, such as acetic acid, propionic acid, glycolic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-amino-salicylic acid, 2-phenoxybenzoic acid, 2- or 1,2-naphthalenedisulfonic acid.

The term "salts" also includes metal complexes of the two basic components I and II. Those complexes may apply, as desired, to only one component or to both components independently. It is also possible to prepare metal complexes that combine the two active ingredients I and II with each other to form a mixed complex.

In practice, the active ingredients I and II are advantageously used in the form of free bases, to which other agrochemically active substances, such as insecticides, acaricides, nematicides, herbicides, growth regulators and fertilisers, and especially other microbicides, may be added.

Advantageous mixing ratios of the two active ingredients are

I:IIA=20:1 to 1:20, preferably 10:1 to 1:10 and 3:1 to 1:1;
I:IIB=1:20 to 10:1, preferably 1:10 to 1:1 and 1:5 to 1:2.

The active ingredient mixtures I+II according to the invention have very advantageous properties for protecting plants against disease infestation.

The active ingredient mixtures in question can be used to inhibit or destroy the microorganisms which occur on plants or on parts of plants (the fruit, blossom, leaves, stems, tubers or roots) of different crops of useful plants, while at the same time parts of plants that grow later are also protected against such microorganisms. They can also be used as dressings in the treatment of plant propagation material, especially seed (fruit, tubers, grains) and plant cuttings (e.g. rice), to provide protection against fungus infections as well as against phytopathogenic fungi which occur in the soil. The active ingredient mixtures according to the invention are distinguished by the fact that they are especially well tolerated by plants and are environmentally friendly.

The active ingredient mixtures are effective against phytopathogenic fungi belonging to the following classes: Ascomycetes (e.g. Venturia, Podosphaera, Erysiphe, Monilinia, Mycosphaerella, Uncinula); Basidiomycetes (e.g. the genus Hemileia, Rhizoctonia, Puccinia); Fungi imperfecti (e.g. Botrytis, Helminthosporium, Rhynchosporium, Fusarium, Septoria, Cercospora, Alternaria, Pyricularia and Pseudocercosporella herpotrichoides); Oomycetes (e.g. Phytophthora, Peronospora, Bremia, Pythium, Plasmopara).

Target crops for the areas of indication disclosed herein comprise within the scope of this invention e.g. the following species of plants: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). This list does not represent any limitation.

The active ingredient mixtures according to the invention are especially advantageous for use in a) I+IIA for the treatment of pomes and stone fruit, especially apples, against Sphaeroteca, Monilinia, Venturia and Podosphaera;

b) I+IIB for the treatment of vines, vegetables and berries against Botrytis and Alternaria.

The mixtures of compounds of formulae I and II are normally used in the form of compositions. The compounds of formulae I and II can be applied to the area or plant to be treated either simultaneously or in succession on the same day, if desired together with further carriers, surfactants or other application-promoting adjuvants customarily employed in formulation technology.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilisers.

A preferred method of applying an active ingredient mixture comprising at least one of each of the active ingredients I and II is application to the parts of the plants that are above the soil, especially to the leaves (foliar application). The frequency and rate of application depend upon the biological and climatic living conditions of the pathogen. The active ingredients can, however, also penetrate the plant through the roots via the soil or via the water (systemic action) if the locus of the plant is impregnated with a liquid formulation (e.g. in rice culture) or if the substances are introduced in solid form into the soil, e.g. in the form of granules (soil application). In order to treat seed, the compounds of formulae I and II can also be applied to the seeds (coating), either by impregnating the tubers or grains with a liquid formulation of each of the active ingredients in succession, or by coating them with an already combined wet or dry formulation. In addition, in special cases, other methods of application to plants are possible, for example treatment directed at the buds or the fruit trusses.

The compounds of the combination are used in unmodified form or, preferably, together with the adjuvants conventionally employed in formulation technology, and are therefore formulated in known manner e.g. into emulsifiable concentrates, coatable pastes, directly sprayable or dilutable solutions, dilute emulsions, wettable powders, soluble powders, dusts, granules, or by encapsulation in e.g. polymer substances. As with the nature of the compositions, the methods of application, such as spraying, atomising, dusting, scattering, coating or pouring, are chosen in accordance with the intended objectives and the prevailing circumstances. Advantageous rates of application of the active ingredient mixture are generally from 50 g to 2 kg a.i./ha, especially from 100 g to 1000 g a.i./ha, more especially from 250 g to 700 g a.i./ha. In the case of the treatment of seed, the rates of application are from 0.5 g to 1000 g, preferably from 5 g to 100 g, a.i. per 100 kg of seed.

The formulations are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g. especially dolomite or pulverised plant residues.

Depending upon the nature of the compounds of formulae I and II to be formulated, suitable surface-active compounds are non-ionic, cationic and/or anionic surfactants having good emulsifying, dispersing and wetting properties. The term "surfactants" will also be understood as comprising mixtures of surfactants.

Particularly advantageous application-promoting adjuvants are also natural or synthetic phospholipids of the cephalin and lecithin series, e.g. phosphatidylethanolamine, phosphatidylserine, phosphatidylglycerol and lysolecithin.

The agrochemical compositions normally comprise 0.1 to 99%, especially 0.1 to 95%, compounds of formulae I and II, 99.9 to 1%, especially 99.9 to 5%, of a solid or liquid adjuvant and 0 to 25%, especially 0.1 to 25%, of a surfactant.

Whereas commercial products will preferably be formulated as concentrates, the end user will normally employ dilute formulations.

The Examples which follow serve to illustrate the invention, "active ingredient" denoting a mixture of compound I and compound II in a specific mixing ratio.

FORMULATION EXAMPLES

| Wettable powders | a) | b) | c) |
|---|---|---|---|
| active ingredient [I:II = 1:3(a), 1:2(b), 1:1(c)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| active ingredient (I:II = 1:6) | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| active ingredient [I:II = 1:6(a), 1:2(b), 1:10(c)] | 5% | 6% | 4% |
| talcum | 95% | — | — |
| kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
| --- | --- |
| active ingredient (I:II = 2:1) | 15% |
| sodium lignosulfonate | 2% |
| carboxymethylcellulose | 1% |
| kaolin | 82% |

The active ingredient is mixed and ground with the adjuvants, and the mixture is moistened with water. The mixture is extruded and then dried in a stream of air.

| Coated granules | |
| --- | --- |
| active ingredient (I:II = 1:10) | 8% |
| polyethylene glycol (mol. wt. 200) | 3% |
| kaolin | 89% |

The finely ground active ingredient is uniformly applied, in a mixer, to the kaolin moistened with polyethylene glycol. Non-dusty coated granules are obtained in this manner.

| Suspension concentrate | |
| --- | --- |
| active ingredient (I:II = 1.8) | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% emulsion in water) | 1% |
| water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20–22; 1967):

ppm=milligrams of active ingredient (=a.i.) per liter of spray mixture

X=% action by active ingredient I using p ppm of active ingredient

Y=% action by active ingredient II using q ppm of active ingredient.

According to Colby, the expected (additive) action of active ingredients I+II using p+q ppm of active ingredient is $$E = X + Y - \frac{X \cdot Y}{100}$$

If the action actually observed (O) is greater than the expected action (E), then the action of the combination is superadditive, i.e. there is a synergistic effect.

EXAMPLE B-1

Residual-protective action against *Venturia inaegualis* on apples

Apple cuttings with 10–20 cm long fresh shoots are sprayed to drip point with an aqueous spray mixture prepared from a wettable powder formulation of the active ingredient mixture and infected 24 hours later with a conidia suspension of the fungus. The plants are incubated for 5 days at 90–100% relative humidity and stood in a greenhouse for a further 10 days at 20–24° C. Fungus infestation is evaluated 12 days after infection.

EXAMPLE B-2

Action against *Botrytis cinerea* on apple fruits

Artificially damaged apples are treated by dropping a spray mixture of the active ingredient mixture onto the damage sites. The treated fruits are then inoculated with a spore suspension of the fungus and incubated for one week at high humidity and about 20° C. The fungicidal action of the test compound is derived from the number of damage sites that have begun to rot.

EXAMPLE B-3

Action against *Podosphaera leucotricha* on apple shoots

Apple cuttings with about 15 cm long fresh shoots are sprayed with a spray mixture of the active ingredient mixture. The treated plants are infected 24 hours later with a conidia suspension of the fungus and placed in a climatic chamber at 70% relative humidity and 20° C. Fungus infestation is evaluated 12 days after infection.

The mixtures according to the invention exhibit good activity in these Examples.

EXAMPLE B-4

Action against *Drechslera teres* on barley 10-day-old barley plants of the "Golden Promise" variety are sprayed with a spray mixture of the active ingredient mixture. The treated plants are infected 24 hours later with a conidia suspension of the fungus and incubated in a climatic chamber at 70% relative humidity and 20–22° C. Fungus infestation is evaluated 5 days after infection.

Component I: cyprodinil; component IIA: myclobutanil.

Results: see Table B-4

TABLE B-4

| | mg a.i. per litre (ppm) | | | % action | | SF |
| --- | --- | --- | --- | --- | --- | --- |
| Test No. | a.i. I | a.i. IIA | I:II | O (found) | E (expected) | O/E |
| 1 | 0.02 | | | 2 | | |
| 2 | 0.06 | | | 13 | | |
| 3 | 0.2 | | | 19 | | |
| 4 | 0.6 | | | 24 | | |
| 5 | 2 | | | 46 | | |
| 6 | | 0.006 | | 0 | | |
| 7 | | 0.02 | | 0 | | |
| 8 | | 0.06 | | 0 | | |
| 9 | | 0.2 | | 10 | | |
| 10 | | 0.6 | | 16 | | |
| 11 | | 2 | | 21 | | |
| 12 | | 6 | | 38 | | |
| 13 | 0.02 | 0.006 | 3:1 | 5 | 2 | 2.5 |
| 14 | | 0.02 | 1:1 | 8 | 2 | 4.0 |
| 15 | | 0.06 | 1:2 | 8 | 2 | 4.0 |
| 16 | 0.06 | 0.006 | 10:1 | 35 | 13 | 2.7 |
| 17 | | 0.02 | 3:1 | 43 | 13 | 3.3 |
| 18 | | 0.06 | 1:1 | 43 | 13 | 3.3 |
| 19 | | 0.2 | 1:3 | 57 | 22 | 2.6 |
| 20 | | 0.6 | 1:10 | 81 | 27 | 3.0 |

TABLE B-4-continued

| Test No. | mg a.i. per litre (ppm) a.i. I | mg a.i. per litre (ppm) a.i. IIA | I:II | % action O (found) | % action E (expected) | SF O/E |
|---|---|---|---|---|---|---|
| 21 | 0.2 | 0.02 | 10:1 | 67 | 18 | 3.8 |
| 22 |  | 0.06 | 3:1 | 67 | 18 | 3.8 |
| 23 |  | 0.2 | 1:1 | 73 | 27 | 2.7 |
| 24 |  | 0.6 | 1:3 | 81 | 32 | 2.5 |
| 25 |  | 2 | 1:10 | 74 | 36 | 2.1 |
| 26 | 0.6 | 0.06 | 10:1 | 62 | 24 | 2.6 |
| 27 |  | 0.2 | 3:1 | 67 | 32 | 2.1 |
| 28 |  | 0.6 | 1:1 | 70 | 36 | 1.9 |
| 29 |  | 2 | 1:3 | 81 | 40 | 2.0 |
| 30 |  | 6 | 1:10 | 62 | 53 | 1.2 |

What is claimed is:

1. A method for treating pome plants infested with Venturia and Podoshpearea spp., comprising applying to said plant, plant parts, seeds or their surrounding a composition comprising a synergistically fungicidally effective amount of a mixture of at least two active ingredient components together with a suitable carrier, wherein component I is cyprodinil of formula I

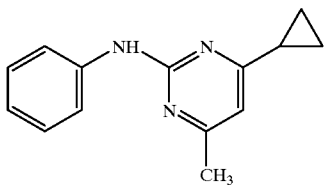

and wherein component II is myclobutanil, and wherein the weight ratio of I:II is from 10:1 to 1:10.

2. A method according to claim 1, wherein the plants, parts of plants, seeds or their surroundings are treated with a composition comprising component I and a component II according to claim 1, in any desired sequence or simultaneously.

* * * * *